United States Patent [19]

Spiegel

[11] Patent Number: 4,837,154
[45] Date of Patent: Jun. 6, 1989

[54] SELECTIVE GROWTH MEDIUM FOR ISOLATION OF MOBILUNCUS FROM VAGINAL FLUID

[75] Inventor: Carol A. Spiegel, Madison, Wis.

[73] Assignee: Wisconsin Alumni Research Foundation, Madison, Wis.

[21] Appl. No.: 3,116

[22] Filed: Jan. 14, 1987

[51] Int. Cl.$^4$ .......................... C12N 1/20; C12Q 1/10; C12R 1/36
[52] U.S. Cl. ................................. 435/253.6; 435/38; 435/871
[58] Field of Search ..................... 435/29, 34, 38, 253, 435/871

[56] References Cited

PUBLICATIONS

E. Hjelm, et al. (1984), "Primary Isolation of Curvest Rods from Women With Vaginal Discharge," Scand. J. Nephrol. Urol., Suppl. 86, 113–116.

E. Holst, et al. (1984), "Anaerobic Curved Rods in Genital Samples of Women," Scand. J. Nephrol. Urol., Suppl., 86, 117–124.

J. L. Thomason, et al. (1984), "A Selective and Differential Agar for an Anaerobic Comma-shaped Bacteria Recovered from Patients Having Motile Rods and Non-specified Vaginosis," Scand. J. Nephrol. Urol., Suppl., 86, 125–128.

A. Fox, et al. (1984),: "Two Curved Rods in Non-Specific Vaginitis," Scand. J. Nephrol. Urol., Suppl., 86, 93–96.

C. Pahlson, et al. (1984), "Numerical Taxonomy of Motile Anaerobic Curved Rods Isolated from Vaginal Discharge," Scand. J. Nephrol. Urol., Suppl., 86, 251–256.

M. Sprott, et al. (1984), "Motile Curved Bacilli," Scand. J. Nephrol. Urol., Suppl, 86, 107–111.

A. J. Taylor, et al. (1984), "Morphological and Chemical Characteristics of an Aerobic Curved Rod-Shaped Bacteria From the Female Genital Tract," Scand. J. Nephrol. Urol., Suppl., 86, 97–106.

M. Sprott, et al. (1983), "Characteristics of Motile Curved Rods in Vaginal Secretions," J. Med. Mocrobiol., 16, 175–182.

C. Pahlson, et al. (1983), "Characterization of Motile Anaerobic Curved Rods Isolated from Women with Lower Genital Tract Infection in Three Different Countries," Eur. J. Sex. Transm., 73–75.

E. Holst, et al. (1982), "Characteristics of Anaerobic Comma-Shaped Bacteria Recovered from the Female Genital Tract," Eur. J. Clin. Microbiol., 1, 310–116.

A. Skarin, et al. (1983), "Antimicrobial Susceptibility of Comma-shaped Bacteria Isolated from the Vagina," Scand. J. Infect. Dis., Suppl., 40, 81–84.

E. Holst, et al. (1983), "Anaerobic comma-shaped Bacteria Recovered from the Human Genital Tract, A Review," Scand. J. Infect. Dis., Suppl. 40, 23–30.

Primary Examiner—Elizabeth C. Weimar
Assistant Examiner—Joan Ellis
Attorney, Agent, or Firm—David J. Houser; Nicholas J. Seay

[57] ABSTRACT

A selective growth medium for the isolation of Mobiluncus includes a medium base including an aqueous preparation of a gelling agent and a nutrient broth effective for culturing Mobiluncus. The selective growth medium of the invention further includes a first antimicrobial agent in effective antimicrobial amounts, the antimicrobial agent being selected from the group consisting of colistin, nalidixic acid, and combinations of colistin and nalidixic acid, the colistin having a concentration less than 32 micrograms/ml and the nalidixic acid having a concentration less than 100 micrograms/ml. Tinidazole is included as a second antimicrobial agent in effective, antimicrobial amounts not greater than 1.0 micrograms/ml. Nile Blue A is also included in *Gardnerella Vaginalis* inhibiting concentrations.

7 Claims, No Drawings

SELECTIVE GROWTH MEDIUM FOR ISOLATION OF MOBILUNCUS FROM VAGINAL FLUID

This invention was made with United States government support awarded by the National Institutes of Health (NIH), Grant #: AI22290. The U.S. government has certain rights in this invention.

TECHNICAL FIELD

The present invention relates to selective growth media for the isolation of bacteria and, in particular, to a selective growth medium for the isolation of Mobiluncus from inocula including common human vaginal flora.

BACKGROUND OF ART

Mobiluncus is a genus of anaerobic curved rod-shaped bacteria that typically is not found in healthy patients but is found in vaginal secretions of many patients with a clinical diagnosis of bacterial vaginosis, formerly called "nonspecific vaginitis" (hereinafter sometimes referred to simply as "vaginosis" or "bacterial vaginosis"). In some references, Mobiluncus is referred to as "curved rods," "anaerobic vibrios," or "comma-shaped" bacteria found as part of the vaginal flora.

It is not established that Mobiluncus is the sole cause of vaginosis, even in those cases in which Mobiluncus is found in the vagina. Other changes also occur in the vaginal flora present in the vaginosis patient. In contrast to what is found in a woman without vaginosis, the bacterial flora typical of vaginosis contains less lactobacilli and more anaerobic bacteria, of which Mobiluncus is only one.

In addition to Mobiluncus, the faculative bacterium Gardnerella vaginalis characteristically is present in the vagina of the vaginosis patient and has also been discussed as a possible causal agent of vaginosis, either by itself or in conjunction with one or more species of Mobiluncus or other anaerobic genera. Gardnerella vaginalis and other competing flora tend to grow faster in culture than does Mobiluncus, making isolation of Mobiluncus by strictly mechanical techniques difficult and even impossible in some instances. These problems have interfered with attempts to routinely isolate Mobiluncus as part of diagnostic procedures.

Those skilled in the art have not been able to selectively culture Mobiluncus with satisfactory success. As a consequence, E. Hjelm, et al. (1984), "Primary Isolation of Curved Rods from Women With Vaginal Discharge," Scand. J. Nephrol. Urol., Suppl. 86, 113–116, report resorting to a dilution and sampling technique for primary isolation and identification of Mobiluncus.

A selective culture medium has been proposed by E. Holst, et al. (1984), "Anaerobic Curved Rods in Genital Samples of Women," Scand. J. Nephrol. Urol., Suppl., 86, 117–124. The selective medium of Holst, et al. includes Columbia agar containing one microgram/ml tinidazole in combination with either colistin (10 microgram/ml) or nalidixic acid (15 microgram/ml). The instant inventors find this concentration of tinidazole sufficiently high to inhibit some strains of Mobiluncus mulieris. Furthermore, the suppression by this medium of Gardnerella vaginalis reported by Holst, et al. could not be reproduced by the instant inventors. It is not known if differences in the strains of Gardnerella vaginalis used or in reagents or techniques account for the different results, but, in any event, Gardnerella vaginalis remained as an importantly interfering organism. Holst, et al. reported at page 123 of their study that Mobiluncus (identified by Holst, et al. simply as "anaerobic curved rods") was never found in the absence of Gardnerella vaginalis, which was consistent with their past experience. This emphasizes the significance of Gardnerella vaginalis as a pervasive and important interfering organism.

J. L. Thomason, et al. (1984), "A Selective and Differential Agar for an Anaerobic Comma-shaped Bacteria Recovered from Patients Having Motile Rods and Non-specific Vaginosis," Scand. J. Nephrol. Urol., Suppl., 86, 125–128, report the development of an agar on which Mobiluncus grows well, with competing bacteria being either suppressed or rendered visually distinguishable fom the Mobiluncus by use of Gram stain. Thus, Columbia CNA agar was used as the basal medium because it was one of the media tested that supported maximal growth of Mobiluncus and was at the same time inhibitory to gram-negative organisms. Ten microgram/ml colistin and 15 microgram/ml nalidixic acid were included in the agar, Mobiluncus consistently showing resistance to those antibiotics in those concentrations. Fetal calf serum added to the agar further enhanced growth of Mobiluncus colonies, albeit the growth of other, competing gram-positive organisms also remained possible. Instead of inhibiting these competing organisms, Thomason, et al., attempted to render them visually distinctive. This was done by adding rabbit blood to the agar. The large species of Mobiluncus caused beta-hemolysis in the rabbit blood medium. Two species of Mobiluncus exist, M. mulieris and M. curtisii (respectively sometimes referred to as "large" and "small" or "long" and "short" curved rods), and Thomason has privately informed the instant inventors that only M. mulieris caused beta-hemolysis. Garnerella vaginalis also flourished and produced beta-hemolysis. However, Gardnerella vaginalis was visually differentiated from the Mobiluncus by Gram stain.

Various culture media have been reported to be effective for the culturing of Mobiluncus, independent of the question of selective culturing. A. Fox et al. (1984), "Two Curved Rods in Non-Specific Vaginitis," Scand. J. Nephrol. Urol., Suppl., 86, 93–96, report the use of Columbia agar with five percent horse blood and, alternatively, brain heart infusion agar plus hemin, vitamin $K_1$, five percent horse blood, and 10 mg/l vancomycin. The reported use of vancomycin here is believed to be a confusion in the text. Other media for the effective cultivation of Mobiluncus are cited by E. Hjelm, et al. (1984), "Primary Isolation of Curved Rods from Women with Vaginal Discharge," Scand. J. Nephrol. Urol., Suppl., 86, 113–116; C. Pahlson, et al. (1984), "Numerical Taxonomy of Motile Anaerobic Curved Rods Isolated from Vaginal Discharge," Scand. J. Nephrol. Urol., Suppl., 86, 251–256; M. Sprott, et al. (1984), "Motile Curved Bacilli," Scand. J. Nephrol. Urol., Suppl., 86, 107–111; A. J. Taylor, et al. (1984), "Morphological and Chemical Characteristics of an Aerobic Curved Rod-Shaped Bacteria from the Female Genital Tract," Scand. J. Nephrol. Urol., Suppl., 86, 97–106; M. Sprott, et al. (1983), "Characteristics of Motile Curved Rods in Vaginal Secretions," J. Med. Microbiol., 16, 175–182; C. Pahlson, et al. (1983), "Characterization of Motile Anaerobic Curved Rods Isolated from Women with Lower Genital Tract Infection in Three Different Countries," Eur. J. Sex. Transm. Dis., 73–75; E. Holst, et al. (1982), "Characteristics of Anaerobic Comma-Shaped Bacteria Removed from the Female Genital Tract," *Eur. J. Clin. Microbiol.*, 1, 310–116; and A. Skarin, et al. (1983), "Antimicrobial Susceptibility of Comma-shaped Bacteria Isolation from the Vagina," *Scand. J. Infect. Dis., Suppl.*, 40, 81–84.

The media used in these references most frequently was Columbia agar supplemented in various combinations with blood (horse, sheep, human, or mixtures thereof), serum (fetal calf, horse), vitamin $K_1$ (menadione), hemin, yeast extract, colistin, and nalidixic acid. Also used were blood agars and other agars containing heart and brain infusion or other substances, such as yeast extract, liver digest, L-cysteine-HCl, sodium formaldehyde sulphoxylate, hemin, vitamin $K_1$, sodium formate, sodium fumarate, sodium pyruvate, and sodium succinate. E. Holst, et al. (1983), "Anaerobic Comma-shaped Bacteria Recovered from the Human Genital Tract, A Review," *Scand. J. Infect. Dis., Suppl.* 40, 23–30, provides an overview of various such culture media used.

Those skilled in the art are cognizant, then, of various culture media in which Mobiluncus can be grown with success. However, a selective growth medium has not yet been developed that encourages Mobiluncus but also suppresses the growth of *Gardnerella vaginalis* to an effective degree.

BRIEF SUMMARY OF THE INVENTION

The present invention is summarized in that a selective growth medium for the isolation of Mobiluncus includes a medium base including an aqueous preparation of a gelling agent and a nutrient broth effective for culturing Mobiluncus. The selective growth medium further includes a first antimicrobial agent in effective antimicrobial amounts, the antimicrobial agent being selected from the group consisting of colistin, nalidixic acid, and combinations of colistin and nalidixic acid, the colistin having a concentration less than 32 micrograms/ml and the nalidixic acid having a concentration less than 100 micrograms/ml. The selective growth medium further includes a second antimicrobial agent consisting of tinidazole in effective, antimicrobial amounts not greater than 1.0 micrograms/ml. Nile Blue A is also present in *Gardnerella vaginalis* inhibiting concentrations.

A primary object of the invention is to provide a culture medium in which Mobiluncus may be readily cultured.

A second object of the invention is to provide such a culture medium in which many of the vaginal flora characteristic of women exhibiting the symptoms of bacterial vaginosis are suppressed to an extent effective in aiding the isolation of Mobiluncus from vaginal fluids.

Other objects, features, and advantages of the invention will be apparent from the following detailed description of the preferred embodiment of the invention.

DETAILED DESCRIPTION OF THE PREFERRED EMBODIMENT

The selective growth medium of the invention for the isolation of Mobiluncus from vaginal flora has as a medium base an aqueous preparation of a gelling agent and a nutrient broth effective for culturing Mobiluncus. A nutrient broth shall be deemed effective for culturing Mobiluncus if it supports the development of Mobiluncus colonies. The nutrient broth preferred is Columbia broth. Columbia broth is a standard nutrient formulation well known to those skilled in the art and commercially available from several sources. It is described in (1969) *Appl. Micro. Biol.*, 17, 68 and contains per liter:

10 g pantone
10 g bitone
3 g tryptic digest of beef heart
0.1 g L-cysteine HCl
2.5 g dextrose
5 g NaCl
0.1 g $MgSO_4$ (anhydrous)
0.02 g $Fe_2SO_4$
0.6 g $NaCO_3$
0.83 g Tris(hydroxymethyl)aminomethane
2.86 Tris(hydroxymethyl)aminomethane HCl However, a medium base containing the nutrients of Columbia agar, brain heart infusion medium or other nutrient materials capable of supporting Mobiluncus and known to those skilled in the art is also satisfactory. The gelling agent may be agar present in concentrations effective to produce a cohesive gel.

To the medium base is added a first antimicrobial agent in effective antimicrobial amounts, the first antimicrobial agent being selected from the group consisting of colistin, nalidixic acid, and combinations of colistin and nalidixic acid. The colistin must be in a concentration less than 32 micrograms/ml, and the nalidixic acid must be in a concentration less than 100 micrograms/ml. Within these limitations colistin and nalidixic acid may be in any amounts relative to each other. A second antimicrobial agent, tinidazole, is present in effective, antimicrobial amounts but in a concentration not greater than 1.0 micrograms/ml. At a concentration of 1.0 micrograms/ml tinidazole, some strains of *Mobiluncus mulieris* may be inhibited. A tinidazole concentration of 0.6 micrograms/ml is tolerated by all strains of Mobiluncus tested by the inventors and is the concentration necessary to avoid any inhibition. At concentrations less than 0.6 micrograms/ml tinidazole, some of the other species of anaerobes found in bacterial vaginosis were no longer inhibited.

It is preferred that mammalian serum be added to the medium base as a supplement to the nutrient broth. The serum stimulates the growth of Mobiluncus. A serum concentration of about 2% is satisfactory. Horse, sheep, bovine, human, and rabbit sera are examples of satisfactory mammalian sera, rabbit serum being preferred. It is also preferred to add a soluble starch in a concentration of about 1% by weight to enhance Mobiluncus growth. Glycogen or an insoluble starch such as corn starch are less preferred alternatives.

In addition, Nile Blue A is added to the medium base in *Gardnerella vaginalis* inhibiting concentrations. Nile Blue A is one of the biological stains the manufacturing specifications of which have been defined by the Biological Stain Commission of the University of Rochester, Rochester, N.Y. Nile Blue A is available from Eastman Kodak Company, Laboratory and Research Products Division, Rochester, N.Y. 14650, as advertised in its catalog number 52, dated July 1, 1985, pages 366 and 615. Within that catalog, Nile Blue A is given the chemical number C 8679 (Eastman Kodak's own designation) and is identified as C.I. 51180 (the identifying number of the Biological Stain Commission). The Chemical Abstract number is 2381-85-3. Nile Blue A is also commonly referred to as C.I. Basic Blue 12 or as Nile Blue Sulfate. The chemical structure of Nile Blue A is set forth at p. 366 of the Eastman Kodak Company catalog referred to.

Nile Blue A has been discovered to inhibit *Gardnerella vaginalis* with inhibitory effects occurring at Nile Blue A concentrations as low as 50 micrograms/ml. A more reliable inhibitory effect was discovered to occur at a concentration of at least 100 micrograms/ml. Mobiluncus tolerates Nile Blue A up to concentrations at least as high as 200 micrograms/ml with some strains of Mobiluncus tolerating concentrations approaching 1 mg/ml. Consequently, the concentration of Nile Blue A in the selective culture medium of the invention must fall between 50 micrograms/ml and 1 mg/ml and preferably is between 100 micrograms/ml and 200 micrograms/ml.

In addition to the nutrients, antibiotics, and inhibitors referred to above, it is also necessary to add cysteine-HCl or an equivalent reducing agent in quantities sufficient to clear the medium of dissolved, unreduced oxygen. Resazurin solution may be added to the medium in an amount of 1 microgram/ml as an indicator for unreduced oxygen. Such use of a reducing agent and resazurin solution is conventional.

In the clinical trial discussed below, a particular embodiment of the selective growth medium of the invention was prepared as follows. The following ingredients were combined (the company from which certain of the ingredients were obtained is indicated parenthetically).

| | |
|---|---|
| Columbia broth (DIFCO) | 35.0 g |
| Bacto-Agar (DIFCO) | 15.0 g |
| Cysteine-HCl | 0.4 g |
| Soluble starch (DIFCO) | 10.0 g |
| Resazurin solution (11 mg/44 ml) | 4.0 ml |
| Colistin methane sulfonate | 10 micrograms/ml |
| Nalidixic acid | 15 micrograms/ml |
| De-ionized water | 950.0 ml |

These materials were boiled until all solids were dissolved. Then the solution was autoclaved, cooled to 45°–50° C., and preserved under aseptic conditions. To this solution was added aseptically 20.0 ml rabbit serum (GIBCO), tinidazole (ORTHO) in a quantity sufficient to achieve 0.6 microgram/ml, and Nile Blue A (Eastman Kodak—75% dye content, 0.5 g/10 ml) 1.2 ml. Transferred to petri dishes and allowed to cool, the culture medium gelled. For ease of reference, this preparation shall be referred to as "MOBI" agar. The culture plate was reduced over night prior to inoculation in an atmosphere consisting of 80% nitrogen, 10% hydrogen, and 10% carbon dioxide.

Clinical Trial

A study population was obtained composed of women attending the Student Health Center at the University of Wisconsin-Madison, Madison, WI. All of the women were complaining of vaginal discharge, vaginal odor, or both. Each woman had a clinical diagnosis of bacterial vaginosis that had been confirmed by direct Gram stain. Added to this study population were five additional patients with bacterial vaginosis who attended the Family Practice Clinic, Milwaukee County Medical Center, Milwaukee, Wis.

A vaginal fluid specimen was collected from each patient. A non-lubricated speculum was used, and the fluid was collected on cotton swabs. A first swab was used to prepare a slide for direct examination after Gram staining. A second swab was used to collect fluid which was then placed in Amies transport medium (obtained from REMEL). All but six of the samples from both the University of Wisconsin-Madison and the Milwaukee County Medical Center were received for processing within two hours of collection.

The bacteria of the vaginal fluid specimens were cultured in the following way. All procedures were performed in an anaerobic chamber obtained from Coy Laboratory Products, Inc. With respect to each patient, the swab that had been placed in Amies transport medium was transferred to 0.5 ml rabbit serum and vortexed for 15 seconds to create an inoculum suspension. Culture plates were prepared or purchased, with three sets of culture plates containing respectively heart infusion agar (REMEL) (hereinafter "HI"), Columbia CNA with 5% sheep blood (REMEL) (hereinafter "CNA"), and MOBI. Portions of the inoculum suspension were diluted 1:100 and 1:10,000. Culture plates of each of the three different types of culture medium were inoculated within the inoculum suspension by one or both of the following methods. In the first method, each dilution of the inoculum suspension was plated on one of each of the three types of culture medium plates using a spiral plater obtained from Spiral Systems Instruments Inc. In the second method, one drop of the undiluted inoculum suspension was placed on one of each of the three types of culture medium plates and was streaked four ways for isolation.

After 3 and 7 days of incubation at 35±1° C., the culture plates were examined for pinpoint to small (no greater than 1 mm in diameter) transparent colonies. Colonies fitting this description were counted, Gram stained, and, if they contained curved rods, were subcultured and stocked. All other colony types were counted together and called "other flora." Small curved rods that usually stained gram-positive were labeled as Type I and were presumed to be *Mobiluncus curtisii*. Large curved rods that were usually gram-negative were labeled as Type II and were presumed to be *Mobiluncus mulieris*. The identities of Type I and Type II were later confirmed. In the event no isolated colonies contained curved rods, a sweep stain of the area within the culture plate having the heaviest bacterial growth was examined. If curved rods were detected in the sweep stain, this mixture of organisms was streaked for isolation on each of the three types of culture medium, with the cultures examined in the same way as those derived from the inoculation suspension.

Table I, below, compares the three media for recovery of curved rods from vaginal fluid. The results represent seventeen specimens. Three specimens were positive upon examination with Gram stain for curved rods but were culture negative on all three media. One specimen yielded both a Type I and a Type II strain. In that instance, the Type I strain was recovered in culture only on MOBI. With one additional specimen, no curved rods were detected by Gram stain, but a strain of Type I curved rods was obtained on MOBI. In this instance, no such isolate was obtained on the other two media. In one instance a Type I strain that was not recovered on MOBI was seen only on the sweep stain on the HI medium. The Type I strain was subcultured from the HI medium to HI, CNA, and MOBI, whereupon the strain was recovered only on MOBI. Three specimens were not cultured on HI.

TABLE I

Comparison of Three Media For Recovery Of Curved Rods From Vaginal Fluid

| Strains | | No. Recovered on Each Medium/ No. Recovered on Any Medium | | |
|---|---|---|---|---|
| Type | No. | HI | CNA | MOBI |
| I | 9 | 4/8 | 2/9 | 8/9 |
| II | 6 | 3/4 | 3/6 | 6/6 |
| I or II | 15 | 7/13 (58%) | 5/15 (33%) | 14/15 (93%) |

Table II, below, sets forth the quantity of flora other than curved rods recovered from vaginal fluid on the three media. The standard deviations and p values indicated were determined respectively by an analysis of variance repeated measures and Tukey's WSD post hoc test.

TABLE II

Quantity of Flora Other Than Curved Rods Recovered From Vaginal Fluid on Three Media

| | $Log_{10}$ Colony Forming Units | | |
|---|---|---|---|
| | HI | CNA | MOBI |
| Mean (N = 18) | 7.71 | 7.87 | 6.56 |
| Standard Deviation | 1.05 | 1.06 | 1.63 |
| p Value | HI vs CNA | CNA vs MOBI | |
| | $p > .05$ | $p = .001$ | |
| | HI vs MOBI | | |
| | $p = .001$ | | |

From the work described above, it was clear that after three days of incubation of MOBI agar, curved rods produced relatively distinctive pin point to small ($\leq 1$ mm) colonies that were transparent and colorless. The quantities of vaginosis-associated other flora was significantly decreased on MOBI when compared with HI and CNA. Finally, the isolation of curved rods from women with bacterial vaginosis was significantly improved by the use of MOBI as opposed to the use of HI or CNA.

The formulation for MOBI disclosed above stands only as an example of the selective growth medium of the invention, which is more broadly defined and described elsewhere in the disclosure. It will be readily apparent to those skilled in the art that a number of modifications and changes can be made not only in the disclosed particular formulation but also in the invention as more broadly disclosed, all without departing from the spirit and scope of the present invention. Therefore, it is not intended that the invention be limited by the terms of the formulation and other disclosure above but only by the claims set forth below.

What is claimed is:

1. A selective growth medium for the isolation of Mobiluncus comprising:
   (a) a medium base including an aqueous preparation of a gelling agent and a nutrient broth effective for culturing Mobiluncus;
   (b) a first antimicrobial agent in effective antimicrobial amounts, the antimicrobial agent being selected from the group consisting of colistin, nalidixic acid, and combinations of colistin and nalidixic acid, the colistin having in any event a concentration less than 32 micrograms/ml and the nalidixic acid having in any event a concentration less than 100 micrograms/ml;
   (c) a second antimicrobial agent consisting of tinidazole in effective, antimicrobial amounts not greater than 1.0 micrograms/ml; and
   (d) Nile Blue A in *Gardnerella vaginalis* inhibiting concentrations.

2. The selective growth medium of claim 1 wherein the gelling agent is agar and the nutrient broth is Columbia broth.

3. The selective growth medium of claim 1 wherein the nutrient broth includes mammalian serum.

4. The selective growth medium of claim 3 wherein the mammalian serum is rabbit serum.

5. The selective growth medium of claim 1 further comprising at least 1% by weight of soluble starch.

6. The selective growth medium of claim 1 wherein the concentration of Nile Blue A is at least 50 micrograms/ml and no more than 1 mg/ml.

7. The selective growth medium of claim 1 wherein the concentration of tinidazole is not greater than 0.6 micrograms/ml.

* * * * *